US00PP12569P2

(12) United States Plant Patent
Bergman

(10) Patent No.: US PP12,569 P2
(45) Date of Patent: Apr. 23, 2002

(54) CHRYSANTHEMUM PLANT NAMED 'YOCALCUTTA'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/774,372

(22) Filed: Feb. 1, 2001

(51) Int. Cl.[7] ..... A01H 5/00
(52) U.S. Cl. ..... Plt./291
(58) Field of Search ..... Plt./291

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Yocalcutta', characterized by its uniform and upright plant habit; freely branching growth habit; strong stems; dark green and glossy foliage; uniform flowering response; early flowering, eight-week response time; very large decorative-type inflorescences that are about 10.9 cm in diameter; dark soft orange ray florets with yellow apices; and excellent postproduction longevity with plants maintaining good substance and color for at least three weeks in an interior environment.

1 Drawing Sheet

BACKGROUND OF THE INVENTION

The present Invention relates to a new and distinct cultivar of Chrysanthemum plant, botanically known as *Chrysanthemum×morifolium* and hereinafter referred to by the name 'Yocalcutta'.

The new Chrysanthemum is a product of a planned breeding program conducted by the Inventor in Salinas, Calif. The objective of the breeding program is to create new potted Chrysanthemum cultivars that are suitable for year-round production with uniform plant growth habit, desirable inflorescence form and floret colors, fast response time, and excellent postproduction longevity.

The new Chrysanthemum originated from a cross made by the Inventor in March, 1996, in Salinas, Calif., of a proprietary Chrysanthemum seedling selection identified as code number YB-4620, not patented, as the female, or seed, parent with a proprietary Chrysanthemum seedling selection identified as code number YB-4198, not patented, as the male, or pollen, parent. The new Chrysanthemum was discovered and selected by the Inventor as a single flowering plant within the progeny of the stated cross grown in a controlled environment in Salinas, Calif. The selection of this plant was based on its uniform plant growth habit, desirable inflorescence form and floret colors, fast response time, and excellent postproduction longevity. Plants of the new Chrysanthemum differ primarily from plants of the parent selections in ray floret coloration.

Asexual reproduction of the new Chrysanthemum by vegetative tip cuttings was first conducted in Fort Myers, Fla. in July, 1997. Asexual reproduction by cuttings has shown that the unique features of this new Chrysanthemum are stable and reproduced true to type in successive generations.

SUMMARY OF THE INVENTION

The cultivar Yocalcutta has not been observed under all possible environmental conditions. The phenotype may vary somewhat with variations in environment such as temperature, daylength, and/or light level, without, however, any variance in genotype.

The following traits have been repeatedly oserved and are determined to be the unique characteristics of 'Yocalcutta'. These characteristics in combination distinguish 'Yocalcutta' as a new and distinct Chrysanthemum:

1. Uniform and upright plant habit.
2. Freely branching growth habit and strong stems.
3. Dark green and glossy foliage.
4. Uniform flowering response.
5. Typically grown as a disbud-type.
6. Early flowering, eight-week response time.
7. Very large decorative-type inflorescencs that are about 10.9 cm in diameter.
8. Dark soft orange ray florets with yellow apices.
9. Excellent postproduction longevity with plants maintaining good substance and color for at least three weeks in an interior environment.

Plants of the new Chrysanthemum can be compared to plants of the cultivar Dark Bronze Charm, disclosed in U.S. Plant Pat. No. 6,801. In side-by-side comparisons conducted by the Inventor in Salinas, Calif., plants of the new Chrysanthemum differ from plants of the cultivar Dark Bronze Charm in ray floret coloration and in the following characteristics:

1. Plants of the new Chrysanthemum flower more uniformly than plants of the cultivar Dark Bronze Charm.
2. Plants of the new Chrysanthemum have larger inflorescences than plants of the cultivar Dark Bronze Charm.
3. Plants of the new Chrysanthemum have broader ray florets than plants of the cultivar Dark Bronze Charm.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a top perspective view of a typical flowering plant of 'Yocalcutta' grown a disbud-type.

The photograph at the bottom of the sheet comprises a close-up view of typical inflorescences of 'Yocalcutta' grown as a disbud-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the autumn in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 4,000 to 6,000 foot-candles. Four unrooted cuttings were directly stuck in 15-cm containers, exposed to long day/short night conditions, and pinched once about 14 days later. One week after the pinch, the photoinductive short day/long night treatments were started. Plants used for this description were grown as disbud-types. Measurements and numerical values represent averages of typical flowering plants.

Botanical classification: *Chrysanthemum×morifolium* cultivar Yocalcutta.

Commercial clasification: Decorative-type potted Chrysanthemum.

Parentage:

*Female, or seed, parent.*—Proprietary *Chrysanthemum×morifolium* seeding selection identified as code number YB-4620, not patented.

*Male, or pollen, parent.*—Proprietary *Chrysanthemum×morifolium* seedling selection identified as code number YB-4198, not patented.

Propagation:

*Type.*—Terminal tip cuttings.

*Time to initiate roots.*—About four days at 21° C.

*Time to produce a rooted cutting.*—About ten days at 21° C.

*Root description.*—Fibrous and well-branched.

Plant description:

*Appearance.*—Herbaceous decorative-type potted Chrysanthemum typically grown as a disbud-type. Stems upright and outwardly spreading giving a uniformly flat-topped appearance to the plant. Freely branching, about four lateral branches develop after removal of terminal apex (pinching); dense and full plants. Moderate vigor. Relatively compact.

*Plant height.*—About 25.5 cm.

*Plant width.*—About 43 cm.

*Lateral branches.*—Length: About 19.5 cm. Diameter: About 6 mm. Internode length: About 1.3 cm. Strength: Very strong. Texture: Pubescent. Color: 144A to 146A.

*Foliage description.*—Arrangement: Alternate. Quantity of leaves per lateral stem: About 13. Length: About 7.2 cm. Width: About 5.7 cm. Apex: Cuspidate. Base: Mostly truncate. Margin: Palmately lobed, sinuses between lateral lobes parallel to divergent. Texture: Upper and lower surfaces with very fine pubescence; veins prominent on lower surface; leathery. Color: Young foliage, upper surface: Darker than 147A; glossy. Young foliage, lower surface: Darker than 147B. Mature foliage, upper surface: Darker than 147A; glossy. Mature foliage, lower surface: Darker than 147B. Venation, upper surface: 147A. Venation, lower surface: 147B. Petiole length: About 3.2 cm. Petiole diameter: About 3 mm. Petiole color: 147B.

Inflorescence description:

*Appearance.*—Decorative-type inflorescence form with elongated oblong-shape ray florets. Inflorescences borne on terminals above foliage. Disk and ray florets arranged acropetally on a capitulum. Not fragrant. Typically grown as a disbud-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to three weeks of long day/short night conditions followed by photoinductive short day/long night conditions flower about 50 days later when grown during the summer and flower about 55 days later when grown during the winter.

*Postproduction longevity.*—Inflorescences maintain good color and substance for at least three weeks in an interior environment.

*Quantity of inflorescences.*—Produced as a disbud-type, all the lateral inflorescences are removed leaving only the terminal inflorescence.

*Inflorescence bud.*—Height: About 6 mm. Diameter: About 7 mm. Color: Close to 143A.

*Inflorescence size.*—Diameter: Very large, about 10.9 cm. Depth (height): About 3.3 cm. Diameter of disc: About 5.5 mm, inconspicious. Receptacle diameter: About 9 mm.

*Ray florets.*—Shape: Elongated-oblong. Orientation: Initially upright, then about 90° from vertical or perpendicular to the peduncle. Aspect: Initially incurved to flat, than convex. Length: About 5.8 cm. Width: Broad, about 1.5 cm. Corolla tube length: About 5 mm. Apex: Emarginate or acute. Base: Attenuate; short corolla tube. Margin: Entire. Texture: Smooth, glabrous, satiny. Number of ray florets per inflorescence: Numerous, about 222. Color: When opening, both surfaces: 7A to 9A. Fully opened, upper surface: 9A overlain with close to 53A; overall tonality, 34A to 34B, with 9A towards apices. Fully opened, lower surface: 9B to 9C underlain with close to 53A; overall tonality, 34B to 34D.

*Disc florets.*—Arrangement: Masses at center of receptacle, inconspicuous. Shape: Tubular, elongated. Apex: Five-pointed. Length: About 5.5 mm. Width: Apex, about 1.5 mm; base, about 1 mm. Number of disc florets per inflorescence: Less than 20. Color: Immature: 144A to 154A. Mature: Apex: 9A. Mid-section: CLose to 145D. Base: 155D.

*Reproductive organs.*—Androecium: Present on disc florets only. Anther color: 12A. Pollen amount: None. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Yocalcutta', as illustrated and described.

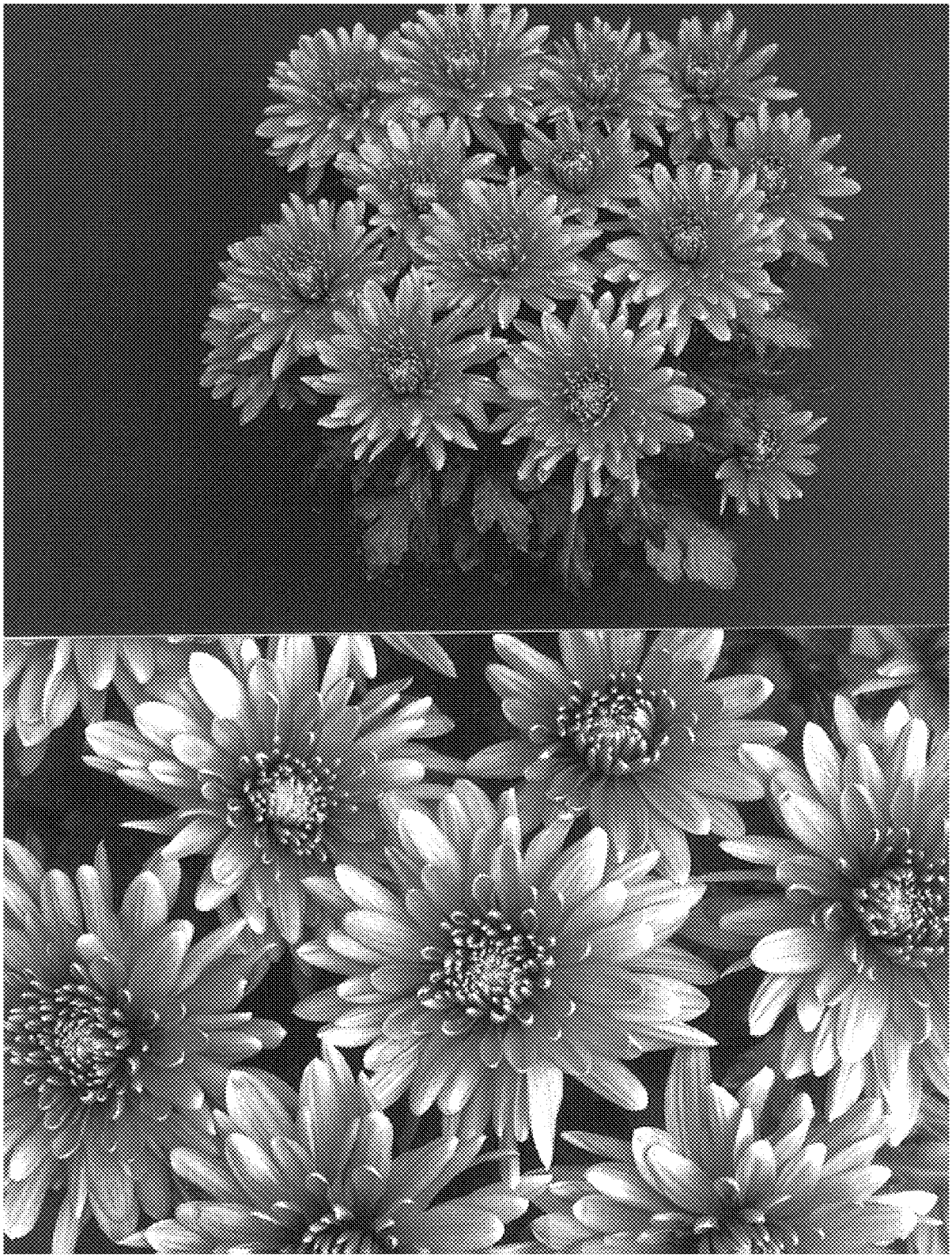

* * * * *